United States Patent [19]

Adams

[11] 4,212,950
[45] Jul. 15, 1980

[54] FERMENTING APPARATUS

[75] Inventor: Robert P. Adams, Walden, N.Y.

[73] Assignee: The Virtis Company, Inc., Gardiner, N.Y.

[21] Appl. No.: 903,594

[22] Filed: May 8, 1978

[51] Int. Cl.[2] ........................................... C12M 1/02
[52] U.S. Cl. .................................. 435/316; 435/284; 435/290
[58] Field of Search ............... 435/284, 290, 313, 315, 435/316; 195/127, 139, 142, 143

[56] References Cited

U.S. PATENT DOCUMENTS

| | | | |
|---|---|---|---|
| 1,235,231 | 7/1917 | Nathan | 195/142 |
| 2,077,652 | 4/1937 | Wessblad et al. | 195/142 X |
| 2,298,561 | 10/1942 | Hendrickson | 195/142 X |
| 2,689,818 | 9/1954 | Fischer | 195/142 X |
| 2,750,328 | 6/1956 | Stimpson et al. | 195/142 |
| 3,625,834 | 12/1971 | Muller | 195/142 X |
| 3,743,582 | 7/1973 | Atsuo Kitai et al. | 195/142 X |
| 3,857,757 | 12/1974 | Herrick et al. | 195/142 |

*Primary Examiner*—R. B. Penland
*Attorney, Agent, or Firm*—Kirkland & Ellis

[57] ABSTRACT

Apparatus providing for the growth of cells in a nutrient bath under controlled conditions includes a pressure vessel with a surrounding dimpled jacket. The pressure vessel is adjustably mounted on three vertical mounting columns, from which it is thermally isolated. Temperature control for the pressure vessel is achieved by a closed heat transfer system which includes a pair of heat exchanger sections in series, one for heating and one for cooling the heat transfer fluid. A removable head or lid for the pressure vessel is lifted by three cables running through a common pulley mounted above the pressure vessel. Impeller blades for agitating the contents of the fermenting apparatus have a drive shaft that extends through the head and is connected to a gear box by a removable driving link. The gear box, and an associated drive motor, are affixed to a common mounting bracket that is pivotable to permit maximum displacement of the head.

6 Claims, 10 Drawing Figures

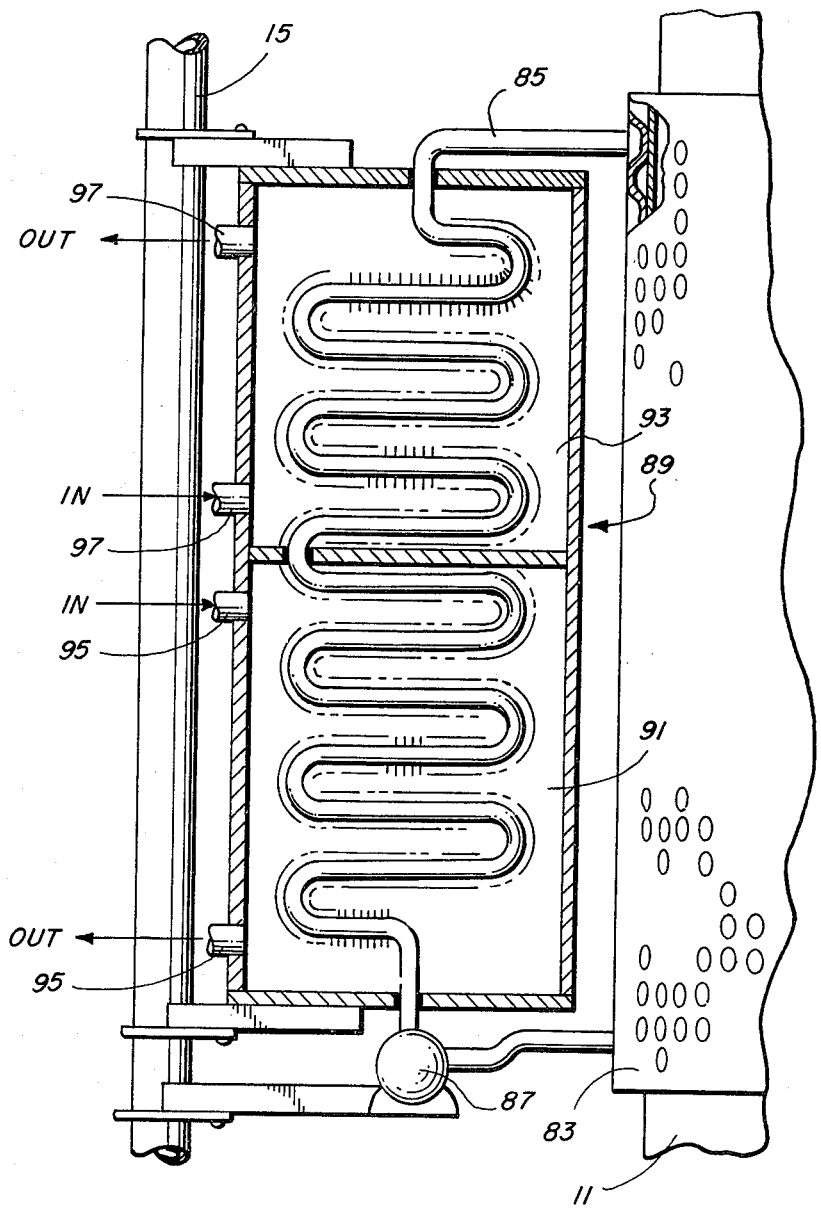

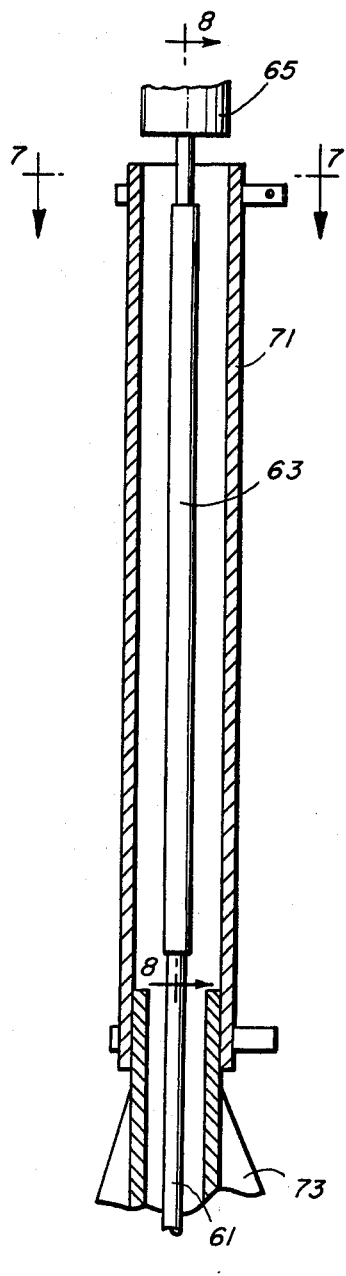
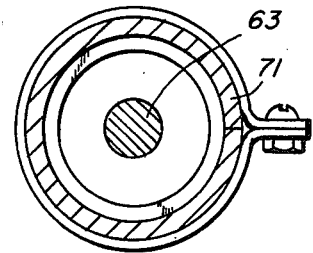
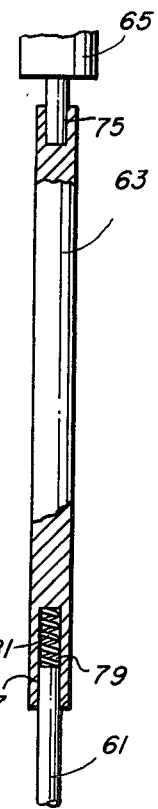
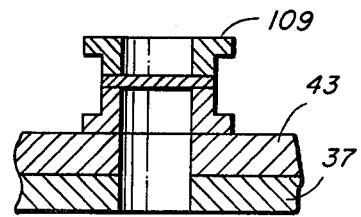
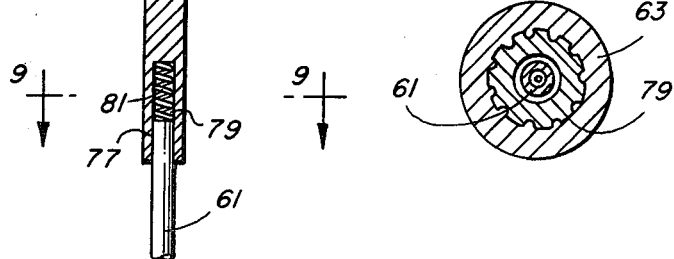

FERMENTING APPARATUS

BACKGROUND OF THE INVENTION

1. Field of the Invention

The present invention generally relates to fermenters utilized in the controlled growth of cells, and more particularly, the present invention relates to a fermenter having the accuracy and range of control of laboratory fermenters and the component accessibility, ruggedness and economy of industrial fermenters.

2. Description of the Prior Art

In the growth of cells or cultures under controlled conditions, it is necessary to have a vessel in which the pressure, temperature and other desired variables may be adjusted as required or desired. Such a pressure vessel must be sterilizable, in order to prevent the intrusion of any undesired cells or organisms. This is frequently done by separate autoclaving, but it is preferable to be able to sterilize in place, especially with large industrial-type fermenting equipment.

In order for the variables to be properly adjusted, it is necessary to have readily accessible control components. Such control components are frequently buried in a complex control panel, making accessibility and replacement difficult. Further, if it is desired to have different control conditions for successive runs of the fermenting equipment, the necessary modifications may involve a major effort.

Another aspect of fermenting equipment is that provision must be made to agitate the nutrient bath in order to obtain the desired dispersion of the cells, as well as to retain introduced gases in solution until they have been absorbed or otherwise utilized by the cells. This means that provision has to be made for driving the impeller blades without interfering with the pressure seal of the pressure vessel or contaminating the contents in any way. A related problem is the mounting of the drive motor on the apparatus. As the mounting structure and the motor are normally located on top of the fermenter, these items present a significant mass on the upper portion of the fermenter with the attendant mechanical and thermal loss problems.

One of the serious defiencies of current industrial-type fermenters is that while they are generally rugged and relatively economical, they involve a very significant weight and size, with the attendant handling problems. In many cases, special large equipment is required for such handling, and the flexibility of the fermenter is very limited. As the mounting of such large devices usually involves heavy heat-conducting-type metals, the thermal conductivity creates difficulties in maintaining desired temperature conditions at the pressure vessel.

Sterilization and temperature control of the pressure vessel is normally achieved by introducing a suitable fluid between the surrounding jacket and the pressure vessel. For sterilization, steam is usually utilized, while tap water would normally be used for cooling purposes. Such an approach leads to tap water contamination, as well as internal scale buildup between the jacket and the vessel, with the resulting loss of temperature control.

As a result of the size and cumbersomeness of conventional industrial fermenters, access to the interior of the pressure vessel is normally quite limited. This creates significant difficulties during the transition from one operating cycle to another, as well as limiting the efficiency of the equipment.

SUMMARY OF THE INVENTION

Many of the deficiencies and problems of prior art fermenters are obviated with the fermenting apparatus of the present invention. This fermenting apparatus introduces into an industrial-style fermenter a flexibility and accuracy of the much smaller laboratory fermenters. While this provides significant advantages for use of the unit in production, it has even greater advantages in pilot-plant applications, where the time, cost and effort of establishing manufacturing procedures can be greatly reduced.

To achieve these results, applicant has provided a large pressure vessel to be mounted on three vertical mounting columns. The bottom of the columns are rigidly secured to one another in a triangular fashion and provided with a solid base support. The pressure vessel is provided with an extending mounting flange about the upper periphery thereof. The pressure vessel is attached to the mounting columns by appropriate mounting brackets that engage the mounting flange on the pressure vessel. These mounting brackets are movable along the mounting columns to adjustably position the pressure vessel at a desired height. Connection between the mounting brackets and the mounting flange on the pressure vessel is through suitable insulating devices, such as asbestos rings. The effect of these insulating asbestos rings is to prevent thermal conduction between the pressure vessel and the mounting columns.

To provide the necessary sterilization and temperature control, a jacket of relatively light gauge material having dimples or indentations is located about a major portion of the pressure vessel. The space between the dimpled jacket and the pressure vessel is part of a closed system for a heat transfer fluid that is pumped through the closed system. Adjustment of the temperature of the heat transfer fluid is achieved by means of a heat exchanger, which includes two separate sections or heat exchangers. The first heat exchanger heats the heat transfer fluid, such as by passing steam over a conduit through which the heat transfer fluid is passed. The second heat exchanger cools the heat transfer fluid, such as by passing tap water over the conduit through which the heat transfer fluid is conveyed.

The heat transfer fluid is pressurized in the closed system, so that it does not change phase (e.g., from a liquid to a gas) as the different heat exchangers are utilized. This is a very significant point, as it provides continuous temperature control from approximately 5° Centigrade to 130° Centigrade. Where a change of phase is involved, there is a discontinuity in the temperature control between approximately 80° and 121° Centigrade. In addition, the use of the pressurized heat transfer fluid (which may be distilled water or distilled water and an ethylene glycol mixture) precludes the development of scale on the inner surface of the jacket and the outer surface of the pressure vessel. As indicated above, such scale adversely effects temperature control. In addition, the potential contamination of the water or condensed steam passed between the jacket and the pressure vessel is not released into the environment.

Obtaining access to the interior of the pressure vessel is realized by means of a removable head or lid on the top of the vessel. This head is normally secured to the top of the vessel, but when it is desired to obtain access to the interior of the vessel, the head may be released and lifted upwardly. This may be achieved by means of three cables secured to the lid at spaced intervals. All three cables run to a common pulley. The mounting columns are interconnected at a point above the top of the pressure vessel by horizontal support members, upon which the pulley and an appropriate pulley motor are mounted.

In order to drive the impeller blades in the interior of the pressure vessel, a drive motor and a gear box are mounted above the top of the pressure vessel. In this particular embodiment, the drive motor and the gear box are both secured to a common mounting bracket that is pivotably rotatably mounted on one of the mounting columns. The gear box is then connected to the shaft of the impeller blades by means of a removable link. The removable aspect of this link is necessary in order to permit raising of the head of the pressure vessel, while the rotatable aspect of the common mounting bracket for the gear box and drive motor permits the gear box to be swung out of the way to permit maximum upward displacement of the lid.

Adjustment of the various variables in the pressure vessel, as well as monitoring of these variables, is necessary. Accordingly, having a readily accessible and easily usable control system has been provided. This control system involves a bank of modular compartments or shelves attached to one of the mounting columns. Each of the modules or shelves is designed for specified control functions, which may be easily modified by substituting a different module. Thus, the fermenting apparatus is very flexible, as well as providing for simple and accurate control of operating conditions.

These and other objects, advantages and features of this invention will hereinafter appear, and for purposes of illustration, but not of limitation, an exemplary embodiment of the subject invention is shown in the appended drawing.

BRIEF DESCRIPTION OF THE DRAWING

FIG. 5 is a schematized partial cross-sectional view of a heat exchanger pursuant to the present invention.

FIG. 6 is a cross-sectional view taken along line 6—6 of FIG. 2.

FIGS. 7 and 8 are cross-sectional views taken along lines 7—7 and 8—8, respectively, of FIG. 6.

FIG. 9 is a cross-sectional view taken along line 9—9 of FIG. 8.

FIG. 10 is a cross-sectional view taken along line 10—10 of FIG. 3.

DETAILED DESCRIPTION OF THE PREFERRED EMBODIMENT

Figure 1:
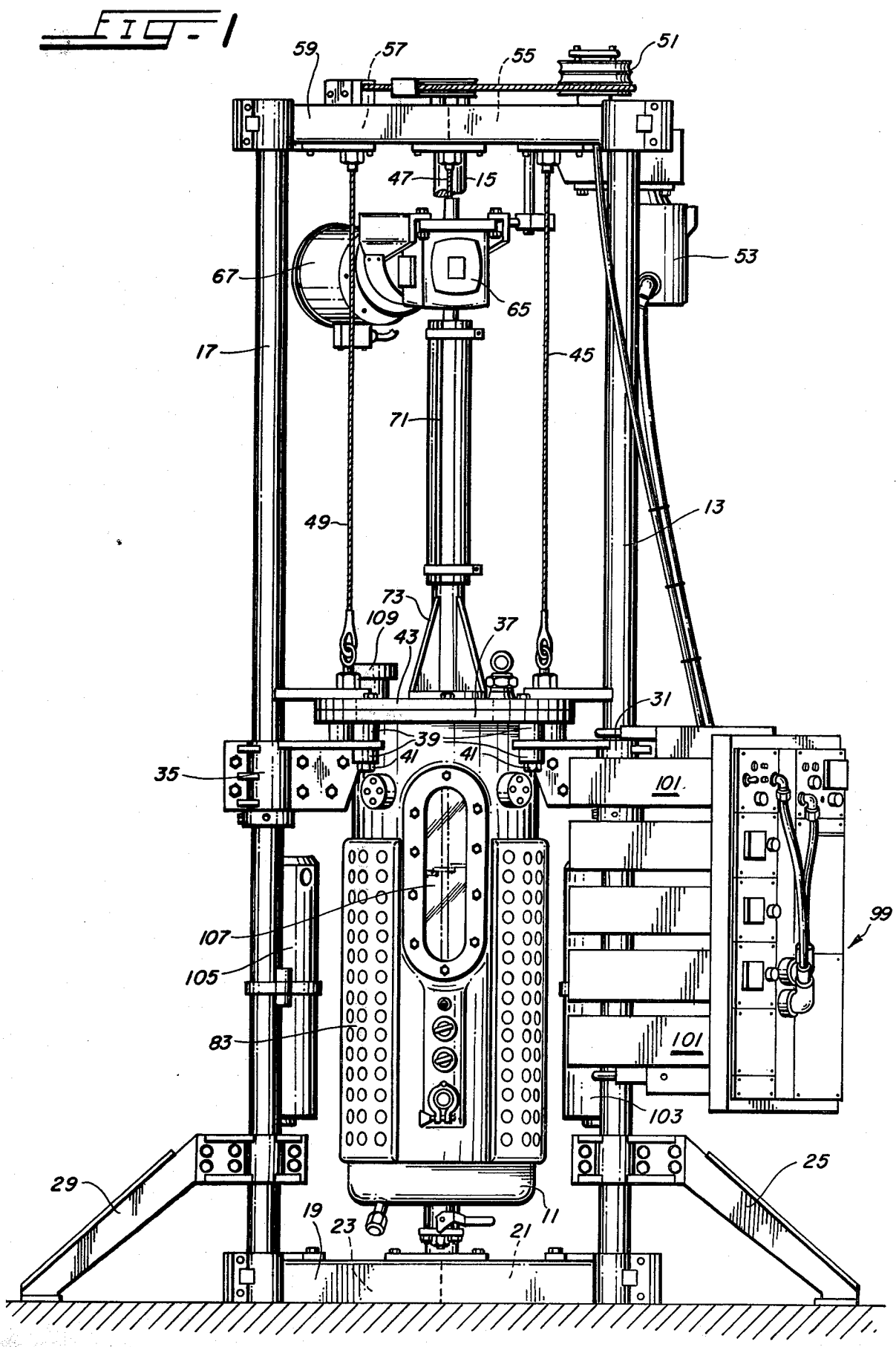
FIG. 1 is a front elevational view of fermenting apparatus in accordance with the present invention.
Figure 2:
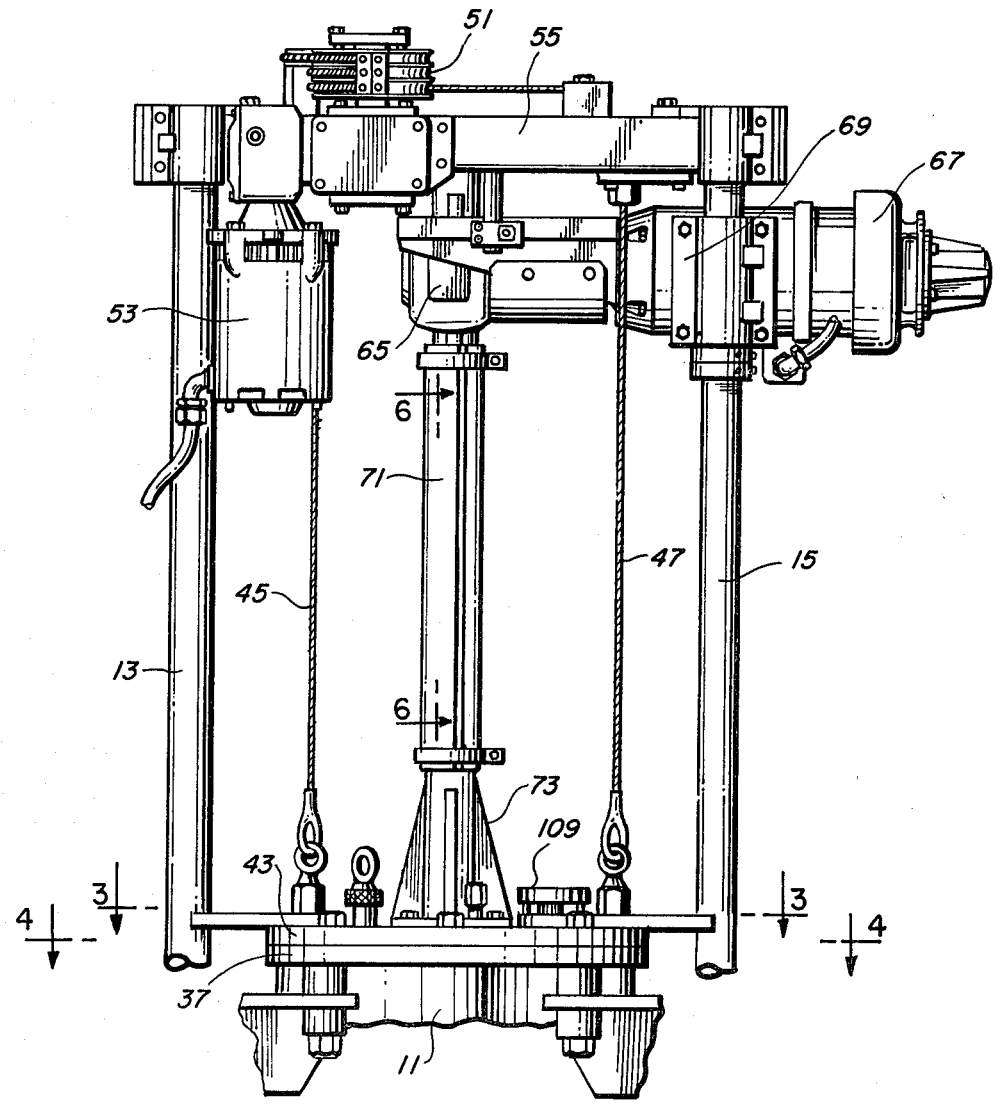
FIG. 2 is an enlarged elevational view of the top portion of the apparatus of FIG. 1.
Figure 3:
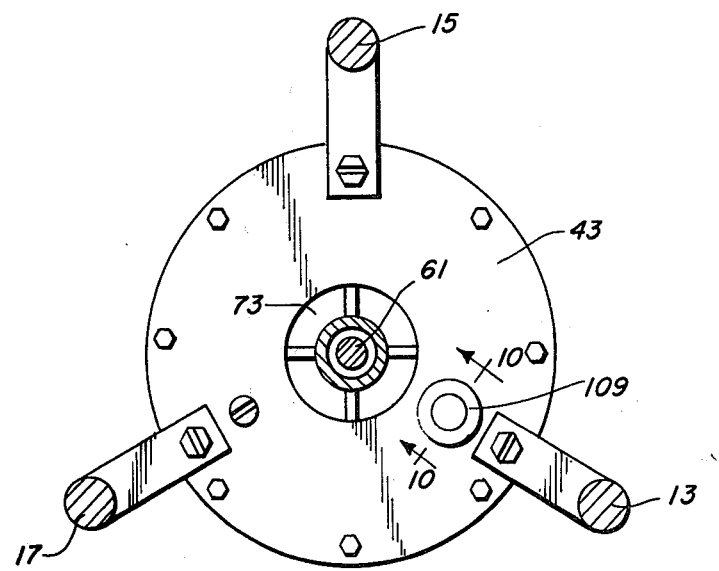
FIGS. 3 and 4 are cross-sectional views taken along lines 3—3 and 4—4, respectively, of FIG. 2.
Figure 4:
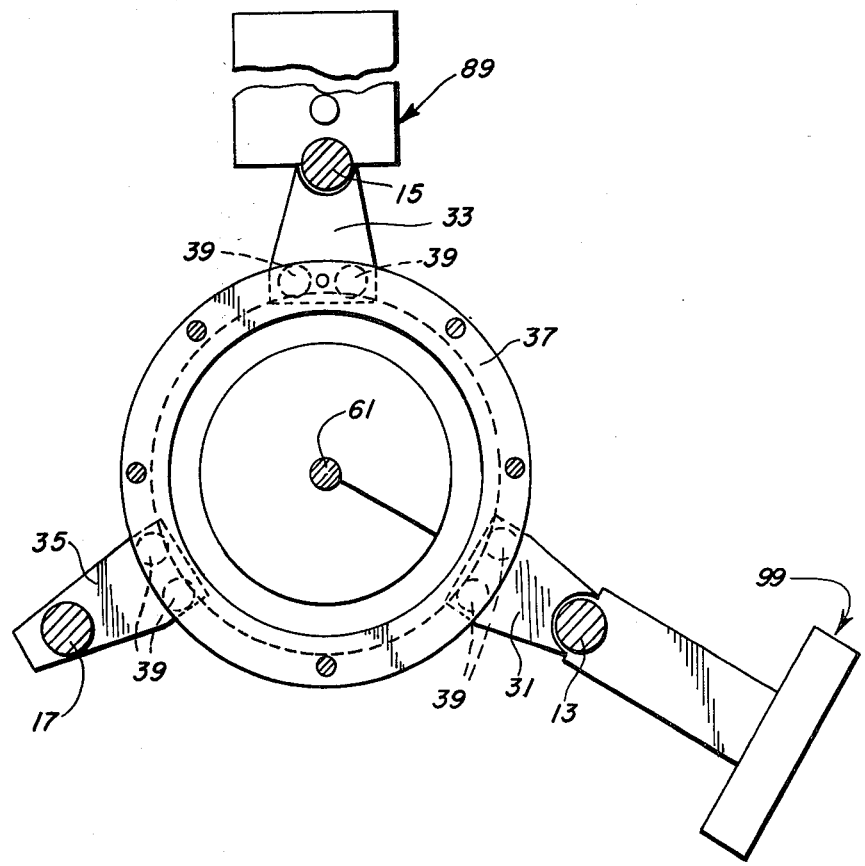

From the drawing, it may be seen that the basic element of the fermenting apparatus is a pressure vessel 11. Pressure vessel 11 has a highly polished interior for maximum resistance to contamination, and its design is such that crevices or blind spots are minimized. Any appropriate type of material may be utilized, of course, but in this preferred embodiment type 316L stainless steel has been employed. If desired, insulation could be located on the exterior of the vessel.

Pressure vessel 11 is mounted on three vertical mounting columns 13, 15 and 17. Columns 13, 15 and 17 are formed of any suitable strong material. The bottoms of the mounting columns are interconnected in a suitable fashion to provide a strong and stable base for the apparatus. In this preferred embodiment, bottom horizontal supports 19, 21 and 23 interconnect the bottoms of the mounting columns in a rigid triangular form. In addition, bracing feet members 25, 27 (not shown) and 29 extend outwardly from the mounting columns and are provided with appropriate feet to provide a secure stance on the floor or other bottom surface.

Mounting brackets 31, 33 (not shown) and 35 are utilized to support pressure vessel 11. These mounting brackets are secured to mounting columns 13, 15 and 17, respectively. Mounting brackets 31, 33 and 35 support pressure vessel 11 by means of a mounting rim or flange 37 about the outer periphery of the top of pressure vessel 11. This mounting flange 37 must be rigidly secured to, or preferably integrally formed with, pressure vessel 11.

Between the mounting brackets 31, 33 and 35 and the mounting flange 37, there is located a thermal insulating material, such as the asbestos rings 39. A similar asbestos ring 39 is placed on the other side of the mounting bracket to permit securing rim 37 to the mounting brackets 31, 33 and 35 by suitable fasteners, such as bolts 41, without providing a thermally conductive path. In this fashion, a pressure vessel 11 is thermally insulated to a considerable degree from the mounting columns 13, 15 and 17, which considerably reduces the temperature control problems caused by heat flow to and from the pressure vessel 11.

Access to the interior of pressure vessel 11 is controlled by a head or lid 43, which abuts the mounting rim 37. In order to lift the lid 43 for opening the pressure vessel, cables 45, 47 and 49 are provided. All three of these cables extend to a common pulley 51, which is actuated by a pulley motor 53. Pulley 51 and pulley motor 53 are mounted on a horizontal support member 55. Horizontal support member 55, and further horizontal support members 57 and 59, are secured to the mounting columns 13, 15 and 17 to provide a triangularly shaped support structure above the vessel 11.

It is necessary to agitate the nutrient fluid and the cells or cultures contained therein in order to obtain the desired distribution of the cells and to maintain introduced gases in solution until they are utilized. For this purpose, suitable impeller blades (not shown) of a conventional nature are located inside the pressure vessel 11. A shaft 61 to drive impeller blades extends upwardly through the head or lid 43. Shaft 61 is connected by a removable drive link 63 to a gear box 65. Gear box 65 is also connected to a drive motor 67. Both gear box 65 and drive motor 67 are mounted on the mounting column 15. Preferably, gear box 65 and drive motor 67 are located on a common mounting bracket 69, which is pivotable about the mounting column 15.

A protective sleeve 71 is releasably secured about the removable drive link 63. Protection sleeve 71 is secured to an upwardly extending structure 73 on the top of head or lid 43. Inside the structure 43, there is located a seal between the impeller drive shaft 61 and the head 43. In order to provide the desired pressure of maintenance and safeguard against contamination, a specially designed duplex rotary seal is utilized. This seal has a seat and face made from the specially formulated abrasion resistant ceramic, which is proven superior to tungsten carbide/tungsten carbide or to carbon/aluminum oxide combinations. It is mounted in an easily removable cartridge through which steam condensate may be continuously pumped for cooling and lubrication. As another alternative, the area between opposing seal faces may be purged with sterile air, giving an extra measure of backup protection against contaminants entering the vessel 11 or the escape of undesirable gases or aerosols to the atmosphere.

Removal of the drive link 63 may be effected by use of spline connections 75 between the removable link 63 and a shaft of gear box 65, and a spline connection 77 between the removable link 63 and impeller shaft 61. A spring 79 is located in a hollowed portion 81 at the bottom of link 63. Spring 79 normally drives the removable link 63 upward toward the gear box 65. However, when it is desired to remove the lid 43 from pressure vessel 11, the protective sleeve 71 may be removed and removable link 63 forced downward against spring 79 a sufficient distance to remove the link from engagement with the gear box shaft, and hence remove link 63 completely from the connection. At the same time, by pivoting gear box 65 and drive motor 67 on mounting 69, it is possible to provide the maximum clearance for raising lid 43. A dimpled jacket 83 is located about a relatively large portion of the pressure vessel 11. Dimpled jacket 83 is made of a relatively light gauge Type 304 stainless steel (although any suitable material could be utilized of course), and provides a sealed space between the jacket and the outer surface of the pressure vessel 11. A conduit 85 connects with the space between the jacket 83 and the vessel 11 to provide a closed system for a heat transfer fluid. Any appropriate type of heat transfer fluid may be used, such as distilled water or a distilled water-ethylene glycol mixture. The heat transfer fluid is pressurized and is pumped through the closed system at a relatively high speed by a pump 87. Pump 87 is appropriately mounted on the mounting column 15.

Use of the dimpled jacket 83 permits the use of less material (i.e., lighter gauge material), provides faster heat transfer, less thermal inertia and reduced steam consumption. These factors result in lower initial and operating costs.

Conduit 85 passes through a heat exchanger 89, which is actually composed of two heat exchangers or heat exchanger portions 91 and 93.

Heat exchanger 89 is shown in schematic form and is only for purposes of illustrating operation, rather than in any specific structural details. In its operational aspects, heat exchanger 91 is utilized to heat the heat transfer fluid, such as by conveying steam into and out of heat exchanger 91 through a conduit 95. Similarly, heat exchanger 93 is utilized to cool the heat transfer fluid by passing a suitable coolant, such as tap water, into and out of the heat exchanger 93 by means of a conduit 97. Suitable valving may also be included for any specific requirements. With this closed system and the dimpled jacket, very accurate temperature control can be achieved without the problem of internal scale buildup or possible tap water contamination.

To provide the desired control, a console 99 is utilized. Console 99 has a plurality of replaceable drawers or modules 101 to provide great flexibility of the control aspects of the structure. In addition, the very easy accessibility of the console and its modules greatly simplify the control aspect of the structure.

Other elements include the sterilizing air filters 103 and 105, mounted on column 13 and 17, respectively.

A suitable viewing window 107 is provided in order to permit visual observation of the fermentation process. A smaller port or window 109 is located in the lid 43 to permit lighting of the interior of the pressure vessel 11 to permit the visual observation. A variety of ports are provided in the pressure vessel 11 to permit the insertion and removal of gases and other elements, as well as test elements to varify operating conditions.

It should be understood that various modifications, changes and variations may be made in the arrangements, operations and details of construction of the elements disclosed herein without departing from the spirit and scope of this invention.

I claim:

1. A fermenting apparatus comprising:
   a fermentation pressure vessel;
   a lid for said pressure vessel that may be opened to gain access to the interior of said vessel;
   an outer jacket surrounding a relatively large proportion of said pressure vessel;
   closed pressurized heat transfer fluid system means located outside the pressure vessel for regulating the temperature in the interior of said fermentation pressure vessel, said closed heat transfer fluid system means including heat transfer fluid for circulating between said closed heat transfer fluid means and the space between said jacket and said fermentation pressure vessel wherein said closed heat transfer fluid system means comprises a first heat exchanger for heating said heat transfer fluid and a second exchanger for cooling said heat transfer fluid, said first and second heat exchangers being connected in series;
   pumping means for circulating the heat transfer fluid of said closed heat transfer fluid system means;
   three vertical mounting columns, said pressure vessel being secured to said mounting columns to rigidly mount said pressure vessel at a spaced interval above an underlying horizontal surface;
   replaceable module control elements for the fermenting apparatus mounted on said mounting columns;
   a drive motor mounted on one of said mounting columns to drive impeller blades in said pressure vessel;
   a gear box mounted on one of said mounting columns to cooperate with said drive motor in driving said impeller blades;
   a drive shaft for the impeller blades in said pressure vessel extending through said lid of said pressure vessel; and
   a drive linkage between said drive shaft and said gear box.

2. A fermenting apparatus as claimed in claim 1 wherein said jacket is dimpled.

3. A fermenting apparatus as claimed in claim 1 wherein:
   steam is utilized in said first heat exchanger to heat said heat transfer fluid; and
   tap water is utilized in said second heat exchanger to cool said heat transfer fluid.

4. A fermenting apparatus as claimed in claim 1 and further comprising:
   three horizontal support members interconnecting said mounting columns above said pressure vessel;
   three cables connected to said lid of said pressure vessel at spaced points thereon;
   a common pulley for said cables mounted on said support members;

a pulley motor mounted on said support members, said pulley motor being operable to raise and lower said lid; and means for disconnecting said drive linkage from said drive shaft and said gear box;

a mounting bracket pivotably mounted to one of said mounting columns, wherein said drive motor and said gear box are mounted on said mounting bracket and are thereby pivotable conjointly with said mounting bracket away from their operating position above said lid when said means for disconnecting said drive linkage is operated to disconnect said drive shaft and said gear box.

5. A fermenting apparatus as claimed in claim 4 wherein said means for disconnecting said drive linkage further comprises:

a spline shaft mounted on said gear box, said spline shaft being driven by said gear box;

a removable link having a first hollowed portion in one end thereof for receiving said spline shaft and a second hollowed portion in the other end for receiving said drive shaft;

a compression spring positioned in said second hollowed portion of said removable link between the end of said drive shaft and the end of said second hollowed portion of said removable link, said compression spring exerting force along the axis of said removable link and normally biasing said removable link in the direction of said spline shaft, thereby maintaining said removable link in a position such that said first hollowed portion engages said spline shaft and said second hollowed portion engages said drive shaft; and wherein said removable link between said spline shaft and said drive shaft is removed by moving said removable link against the bias of said compression spring a sufficient distance to disengage said first hollowed portion of said removable link from said spline shaft.

6. A fermenting apparatus comprising:

a fermentation pressure vessel;

a dimpled outer jacket of relatively light gauge material surrounding a relatively large proportion of said pressure vessel;

a closed heat transfer system including the space between said jacket and said pressure vessel;

pumping means to force a pressurized heat transfer fluid through said heat transfer system, said heat transfer fluid passing between said jacket and said pressure vessel to provide a desired temperature in the interior of said pressure vessel;

three vertical mounting columns interconnected at the bottom ends and having suitable base supports, said pressure vessel being secured to said mounting columns to rigidly mount said pressure vessel at a spaced interval above the horizontal base area;

removable modular control elements attached to said mounting columns in an easily accessible area to provide variable control of temperature and pressure conditions in the fermenting apparatus;

a first heat exchanger to heat said heat transfer fluid mounted on said mounting columns;

a second heat exchanger to cool said heat transfer fluid mounted on said mounting columns, said first and second heat exchangers connected in series with said pumping means to provide a continuous temperature control for said heat transfer fluid and hence said pressure vessel;

a removable lid secured to the top of said pressure vessel to selectively permit access to the interior of said pressure vessel;

three horizontal support members interconnecting said mounting columns above said pressure vessel;

three cables connected to said lid of said pressure vessel at spaced points thereon;

a common pulley for said cables mounted on said horizontal support members;

a pulley motor mounted on said support members, said pulley motor being operable to raise and lower said lid;

a drive motor to drive impeller blades in said pressure vessel;

a gear box cooperating with said drive motor to drive said impeller blades, said drive motor and said gear box secured to one of said mounting columns by a common mounting bracket which is pivotable to clear the space above said pressure vessel to permit maximum displacement of said lid during removal;

a drive shaft for the impeller blades in said pressure vessel extending through said removable lid of said pressure vessel; and a removable drive linkage between said drive shaft and said gear box, said drive linkage being removed during the opening of said lid.

* * * * *